United States Patent

Fuchs

[11] Patent Number: 5,921,444
[45] Date of Patent: *Jul. 13, 1999

[54] DISPENSER PROVIDING TREATMENT SURFACE ENGAGEMENT

[75] Inventor: Karl-Heinz Fuchs, Radolfzell, Germany

[73] Assignee: Ing. Erich Pfeiffer GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/509,439

[22] Filed: Jul. 31, 1995

[30] Foreign Application Priority Data

Aug. 5, 1994 [DE] Germany .............. 94412662 U

[51] Int. Cl.⁶ ................................................. B67D 5/40
[52] U.S. Cl. .................. 222/321.9; 222/385; 604/301
[58] Field of Search .................. 222/321.1, 321.7, 222/321.8, 321.9, 385; 239/373; 604/301, 298, 299, 300

[56] References Cited

U.S. PATENT DOCUMENTS

| | | |
|---|---|---|
| 2,058,515 | 10/1936 | Schaaff ................................ 604/301 |
| 3,314,426 | 4/1967 | Carroll ............................. 604/301 X |
| 3,820,698 | 6/1974 | Franz . | |
| 3,841,533 | 10/1974 | Carroll et al. . | |
| 4,155,489 | 5/1979 | Steiman ............................. 222/321.9 |
| 5,064,420 | 11/1991 | Clarke et al. ..................... 604/301 X |
| 5,154,710 | 10/1992 | Williams . | |
| 5,284,276 | 2/1994 | Cater ................................. 222/321.9 |

FOREIGN PATENT DOCUMENTS

| | | | |
|---|---|---|---|
| 0301615 | 2/1989 | European Pat. Off. ............ 222/321.9 |
| 347084 | 12/1989 | European Pat. Off. . | |
| 2612571 | 9/1988 | France ................................... 604/301 |
| 2143471 | 3/1973 | Germany . | |
| 2142829 | 1/1985 | United Kingdom . | |

*Primary Examiner*—Joseph A. Kaufman
*Attorney, Agent, or Firm*—Quarles & Brady

[57] ABSTRACT

A discharge apparatus, or medium dispenser, has an annular contact surface, face or edge for contacting a surface or object to be sprayed by a medium dispensed from a discharge nozzle spaced therefrom. The contact surface, face or edge can, for example, engage the eye socket around the eye of a patient, the eyelids being eccentrically widened by pressure loading. The contact surface, face or edge is located at the end of the jacket of a cap body into which the medium is discharged by the nozzle. The jacket elastically gives way over part of its length by reason of transverse openings on its circumference and/or bottom. The openings permit a locally, precisely defined incidence of light on the area to be sprayed, and provide non-uniform stiffness.

22 Claims, 1 Drawing Sheet

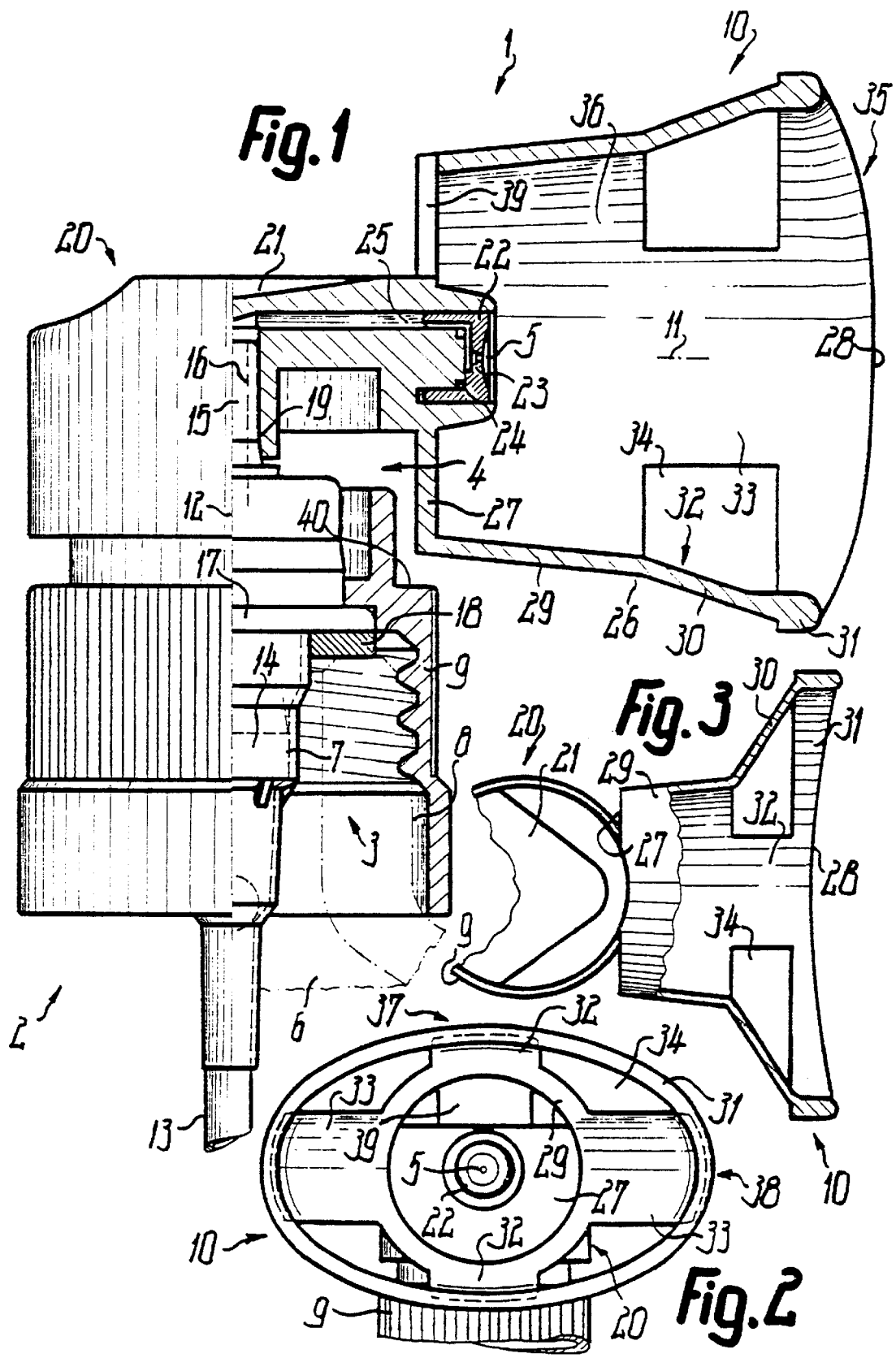

DISPENSER PROVIDING TREATMENT SURFACE ENGAGEMENT

BACKGROUND OF THE INVENTION

1. Field of the Invention

The invention relates to the field of discharge apparatus for treatment media having liquid, pasty, pulverulent and/or gaseous aggregate states during discharge or after discharge. The invention relates more particularly to the field of media dispensers for eyes.

2. Description of Related Art

Dispensers for the kinds of media noted above are used in medical, cosmetic, technical and other similar applications. During such applications, it is frequently appropriate to establish and maintain a certain state or relationship between the part or surface to be treated by the medium and the dispenser, in order to optimize the action of the medium when dispensed. Such media can be used on various kinds of work surfaces and covering layers, including areas and regions of the human body.

The state or relationship which needs to be established between the dispenser and the part to be treated, referred to hereinafter as the treating part, can be one or more of the following: a specific radial and/or axial spacing of the treating part from the medium outlet of the dispenser; a tightening, pretensioning or contraction of the surface or covering layer of the treating part; the extent to which the treating part is ventilated; the illumination or darkening of the treating part; a connection or engagement of the surface of a treating part to contain the dispensed medium, particularly a medium which is atomized as dispensed; a circumferential seal between the dispenser and the surface of the treating part; and, other related states.

SUMMARY OF THE INVENTION

It is an object of the invention to provide a medium discharge apparatus which avoids the disadvantages of known dispensers, which provides the advantage of establishing the special state or relationship between the dispenser and the treating part which optimizes the action of the medium, and which can be embodied in a very simple construction.

In accordance with an inventive arrangement, the discharge apparatus, or medium dispenser, and in particular the medium outlet of the apparatus, is associated with a working member for establishing the state of the treating part to be acted on by the dispensed medium. The working member is preferably positioned in the direction of the medium discharge flow in such a way that it does not influence the flow, or only slightly influences the flow. Thus, the medium flow, which can for example be a very finely atomized spray jet, a concentrated spray jet and/or a droplet, can be supplied from the medium outlet upwardly, downwardly or roughly horizontally in an approximately linear trajectory directly onto the surface of the treating part. Moreover, the treating part can be changed from an initial state to a treating state different than the initial state, by the action or engagement of the working member. Separate working members can be provided in an interchangeable or in a simultaneous multiple arrangement for producing different and particular treating states. Alternatively, a single working member can be configured to produce more than one treating state.

In accordance with the inventive arrangement, the working member surrounds, and so defines a chamber connected to the medium outlet, the working member having a contact surface or edge for engaging the treating part. After the contact surface or edge of the chamber has engaged the treating part, the chamber is effectively enclosed over a partial circumference and/or a partial length of its associated end, so that the dispensed medium cannot disperse out of the chamber, radially, with respect to the axis of the dispensed spray from the medium outlet to the treating part.

The chamber extends from the most inward area adjacent the medium outlet towards the chamber opening, the cross-section of the chamber widening continuously in step-like manner approximately over its entire length, or approximately from the medium outlet to the chamber opening defined by the contact surface or edge. The single circumferential or bottom wall of the chamber can be provided with one or more openings for effecting valve-free ventilation of the chamber. Even in the case of a pressure surge, the one or more openings can provide immediate pressure compensation with respect to the atmospheric pressure of the environment. The one or more openings also permit the treating part to be directly viewed from the outside of the dispenser and from the outside of the surface zone of the treating part to be acted on when the treating state has been achieved.

The working member can be at least partly deformable, and in particular, resiliently elastic. Such resilience is preferably provided in the vicinity of the front contact surface or edge of the jacket or casing defined by the working member and/or the bottom wall. The elasticity can be increased by weakening the cross-section of the material of the working member in partial areas. Such weakening can be provided, for example, by depressions, openings or breaks closed over the entire circumference, so that webs, plates, straps or arm-like bending members are formed. Such bending members can be identical in cross-section or curved differently, or be located in the envelope of the jacket wall defined by the working member connecting in the circumferential direction.

A support for the working member, particularly the discharge head, can be made much more rigid than the discharge head or can be rigid with respect to the operating loads. The support can have, for example, much thicker material cross-sections than the working member. As a result, a rigid support can be constructed in one piece with a component, particularly the working member. The working member can be at least partly deformable in operation in one or more directions at right angles to one another, or can be position-variable with respect to the rigid support.

The discharge feeder can comprise a pouring container, a dropping bottle, a squeezing container and/or a thrust piston pump. The bottle or container can optionally have a narrowed neck or discharge opening. The discharge feeder can be provided for a single discharge of a single medium dose or for repeatedly supplying identical medium doses. In the repeated supply configuration, the discharge pump automatically sucks up further treatment medium after each discharge, from a storage vessel firmly connected thereto.

The discharge apparatus can be formed solely by a one-piece or by a multiple part discharge head or by a unit, which in each case has one or more medium outlets, discharge feeders, discharge actuators and/or medium reservoirs. A multi-part discharge head can have mutually stationary or mutually integral components. The discharge head can be connected with a single connection located in one axis formed by a mandrel and sleeve, or the like, with one of the components of the preassembled unit in a positionally rigid or operation-movable form. The discharge head can also be detachable. In any of the foregoing alternatives, the discharge head may be connected to a medium outlet opening of the component.

A presently preferred embodiment in accordance with the inventive arrangement is particularly suitable for dispensing an eye spray. In this embodiment, the working member forms an eye cup having a contact surface or edge which can engage the edge of an eye socket. In this engaged state, the medium outlet is directed toward the eyeball. The shape of the eye cup can be configured so that the upper and/or lower eyelids can be moved in respective opening directions by the action of the pressure exerted by the eye cup in engaging the edge of the eye socket. The eyelids can be secured in their respective open positions by the continued contact or engagement of the eye cup, so there is no possibility of a reflex-like closing of the eye as a result of the ejected medium jet. At the same time, the working member embodied as an eye cup, precisely defines the distance between the medium outlet and the eyeball or pupil. Openings in the working member provided for ventilation, or defining resilient webs as described above, provide access for light to illuminate the treating part and to view the treating part, in this case the eyeball or pupil, prior to and during dispensing of the treatment medium.

BRIEF DESCRIPTION OF THE DRAWINGS

FIG. 1 is a side elevation of a discharge apparatus, or medium dispenser, partially in section.

FIG. 2 is a partial, right side elevation of FIG. 1, in smaller scale.

FIG. 3 is a top plan of FIG. 1, in smaller scale.

DETAILED DESCRIPTION OF THE PREFERRED EMBODIMENTS

The discharge apparatus, or medium dispenser, 1 is a component of a preassembled discharge unit 2. Discharge unit 2 has in each case single or multiple arrangement devices 3, 4 for feeding a treatment medium and for manually operating the discharge or a device 6 for storing the medium. The medium is delivered into the open by a single medium outlet 5 or by several such medium outlets. The discharge unit 2 can be completely detached from the discharge apparatus 1.

The discharge feeder 3 can be a thrust piston pump 7, which is fixed substantially in the neck 8 of the reservoir or storage vessel 6 with a cap-like fastening 9. Alternatively, the stored supply can be completely located in the pump casing or cylinder. The apparatus 1 forms an end part of the unit 2, which is used for discharge actuation. The apparatus 1 is provided with the medium outlet 5 and a working member 10, positioned downstream therefrom. Accordingly, these parts can, at any time, be subsequently fitted in a functionally correct manner to any other unit 2 at random, provided the unit has appropriate connecting members for the fixing of the parts.

The medium outlet 5 and the working member 10 are parallel to one another, or in alignment along a common axis 11. Axis 11 is at right angles to an axis 12 of the devices 2 through 4 and 6 through 9. Devices 2 through 4 and 6 through 9 are in turn roughly parallel or equiaxial to one another. The pump casing of the pump 7 has an intake channel 13 at the end to be arranged within the reservoir 6. The intake channel 13 can be constructed, for example, as a riser tube by means of which the pump 14 is filled with medium from the reservoir 6 during the return stroke of the pump 7 through a one-way intake valve. The pump piston is displaceable along the cylinder wall of the pump chamber 14 and is provided with a push rod 15 projecting from the other end of the pump casing and displaceable against spring tension. This arrangement enables a precisely determined medium dose to be fed, under pressure, from the pump chamber through an outlet channel 16, and fed both to and from the medium outlet 5, under an over-pressure. An outwardly projecting ring flange 17 of the pump casing serves, together with a seal 18, for sealably pressing the pump casing against the outer, annular front face of the neck 8, with the aid of a screw or crimped cap 9. Cap 9 surrounds the outer circumference of the neck 8 and centers the discharge feeder 3 with respect to the reservoir 6. The push rod 15 forms the sole fastening for the apparatus 1, the working member 10 and the head 20. Head 20 is firmly seated on the outer circumference of the push rod 15, parallel to the axis 12, and with an inner sleeve which contributes to a self-locking force fit 19. Thus, the apparatus 1 can be removed from the unit 2 and the unit 2 can be removed from the reservoir 6 before replacement can take place, all in a non-destructive manner.

The head 20 has an outermost front face forming an actuating handle 21. Actuating handle 21 has the form of an elongated, finger depression. A second such handle, having a size determined by the reservoir 6, is formed by its outer circumference and/or its front or bottom face remote from the handle 21, in such a way that the unit 2 can easily be operated with one hand. The head 20 has roughly the same outside width as the fastening body 9, while the external width of the reservoir 6 is roughly the same or larger than this same outside width and fastening body 9. However, the working member 10 projects over the outer circumference partially or substantially completely in a radial direction, in such a way that there is still sufficient space for the fingers of a hand holding unit 2 between a surface on its end and the outer circumference.

The medium outlet 5 is formed by a very fine atomizing nozzle 23 and has a very small passage located in the axis 11 in the front wall of a cap-like nozzle body 22. Nozzle body 22 has an annular jacket directed toward axis 12, and is inserted radially into a receptacle of the head 20. A nozzle core is disposed in the cap interior of the nozzle body 22. The nozzle core is constructed in one piece with the head 20, and from its front face, engages inside of the front wall of the nozzle body 22. The nozzle core, together with the inner circumferential and front surfaces of the nozzle body 22, form a twisting or whirling device 24. The twisting or whirling device 24 imparts a rotary flow to the medium around the axis 11, during the entry into the inner end of the nozzle channel.

The width of the outer end of the nozzle channel forming the medium outlet 5 can be well below 1 mm or 0.5 mm, particularly if less than 0.1 ml or 0.05 ml of medium is to be discharged during each discharge stroke. The medium outlet appropriately forms the smallest flow cross-section of the outlet channel leading from the pump chamber 14 to the medium outlet. The push rod 15 in the head 20 provides a connection for the medium outlet to a supply channel 25. Supply channel 25 is roughly parallel or eccentric to the axis 11 and is connected to the inner end of the nozzle body 22, and consequently to the twisting device 24. Supply channel 25 is also located on the side of the axis 11 adjacent to the handle 21.

During operation of the medium outlet, an atomized conical jet is discharged under a relatively small pressure. However, the pressure is sufficiently high that the conical jet reaches the end of the working member 10 along an approximately linear path, but does not radially disperse and wet the inner circumference of the working member. A control valve, for example a one-way and/or over-pressure valve displaceable with the piston unit, can be provided between the pump chamber 14 and the medium outlet 5. Alternatively, supply of the medium to the medium outlet 5 can be valve-free as a function of operational requirements, so that the discharge pressure or its pressure characteristic is dependent only on the pressure exerted by manual compression. The discharge volume is determined by the stop limitation of the pump stroke or pump piston, which can strike with its front face against an inner front face of the pump casing. On release, the head 20 moves back again under spring tension and sucks medium out of the reservoir 6.

The cap-like working member 10 has a single jacket 26 and a single bottom wall 27 on the rear end. The front end of the jacket 26 forms an annular, closed end face 28 which does not project into or over the inner circumference of the rest of jacket 26. The disk-like planar bottom 27 is roughly parallel to the axis 12 and is so connected with its radially inner area in one piece manner to the area surrounding the nozzle 23 and the outermost jacket of the head 20, that it forms an extension of the jacket in the circumferential direction. The working member 10 projects both over the outermost front surface or handle 21 of the head 20 and over its front surface remote therefrom. Medium outlet 5 is disposed in a conical radial projection, by means of which medium outlet 5 projects over the outside of the head jacket or the inside of the bottom wall 27 into the working member 10. The amount of the projection is significantly smaller than the length of the working member 10, for example by a factor of one-half, one-fourth or one-fifth of the length.

The jacket 26 has three longitudinally interconnected, different portions 29, 30, 31. Jacket 26 is at least widened in acute-angled manner in each area from the inside of the bottom wall 27 to the portion 31. The longest portion 29 is connected in one piece to the bottom wall 27 and widens over the entire circumference with essentially the same pitch. Portion 26 is two to three times longer than the extent to which medium outlet 5 projects into working member 10. The portion 30 forms an angle with portion 29, and is thicker in axial section and increases in diameter at a different pitch. Portion 30 has two facing circumferential zones widening in acute-angled manner and two outer facing circumferential zones widening in obtuse-angled manner. The final portion 31, forming the end surface 28, has a constant inside width and is much shorter than the portions 29, 30. Portions 29 and 30 have roughly the same wall thickness, but portion 31 is constructed as a thickened torus. The length, along axis 11 of the portions 29, 30 and 31 is in each case smaller than their largest or smallest width or diametric extension along axis 11.

The portions 29 and 31 are closed over their circumference and length, whereas the surface of portion 30 is interrupted. Portion 30 can be provided with several window-shaped openings 34, for example four uniformly circumferentially distributed window-shaped openings 34. Openings 34 together represent more than one-fourth or roughly one-half of the circumference. Openings 34 form longitudinal arms 32 and 33, which are correspondingly uniformly circumferentially distributed, and which can have a smaller length than width. Thus, arms 32 and 33 connect the portions 29 and 31 in an articulated manner and can be cross-sectionally curved in accordance with the associated portion 30. Arms 32 and 33 are resilient and flexible over their length, and provide a resilient bending joint between portions 29 and 31. The strength, that is the relative resilience and rigidity, of the various parts are so chosen that the bottom wall 27 and portion 29 are not significantly deformed, whereas the portions 30 and 31 are deformed in the sense of a widening and/or narrowing. However, in the case of the portion 31, this takes place in such a way that its circumferential dimension does not change or is only slightly changed by resilient elongation.

The portions 29, 30 and 31 extend in the same direction in FIG. 2 and on the outer and inner circumference to the same extent transversely with respect to the axes 11 and 12, namely uniformly elliptically. The space 36 is surrounded by the working member 10, and its end opening 35 defined by the contact surface 28. Thus, space 36 has a corresponding shape with convex, outwardly rounded wide sides 37, and rounded narrow sides 38 having a smaller radius of curvature than sides 37. In the vicinity of the wide sides 37, the much narrower arms 32 are arranged in acute-angled manner relative to the axis 11, whereas the arms 33 in the vicinity of the narrow sides 38 are arranged in obtuse-angled manner relative to the axis 11. In each case, one arm 32 or 33 is connected in the center of the associated side 37, 38 in one-piece manner to the portion 31. The width of the arms 33 can be roughly the same as that of the narrow sides 38. In a view at right angles to the axis 11, the end face 28 is continuously concavely inwardly curved in the vicinity of the wide sides 37, and convexly outwardly curved in the vicinity of the narrow sides 38, the areas passing into one another with continuously curved transitions.

An axial pressure loading against the end face 28 is transferred only via the connection 19 to the unit 2. At the wide sides 37, the axial pressure loading leads to a greater radial widening of the contact surface 28, the portion 31 and the opening 35 than in the vicinity of the narrow sides 38. In the vicinity of the narrow sides 38, the axial pressure loading leads to only a slight, radially inwardly directed narrowing, and the associated arms 32, 33 perform corresponding pivoting movements with respect to the portions 29, 31. The movements of the contact surface 28 are transferred by the slip-free engagement thereof to the associated surface of the treating part, for example an eyelid, which can consequently be spread and kept open in a painless manner. When the treating state is thus achieved, movement of the unit 2 relative to the head 20 performs the delivery stroke. The delivery stroke is appropriately less than 10 mm or 5 mm, and is preferably only about 2 mm to 3 mm. Thus, the medium jet passes out from the rear end of the space 36 along the axis 11, in the direction of the kept-open eye and wets the eyeball with a very fine atomized, low-energy spray jet in a very gentle manner.

Bottom wall 27 can have a window opening 39 which is connected to the top of the outlet projection and/or to the inner circumference of the jacket portion 29. Window opening 39 can be used to influence the medium flow and to influence the orientation of the eyeball during treatment. The window opening 39 provides an illumination zone, towards which the eye can be oriented in an upwardly sloping manner with respect to the axis 11. The upper openings 34 are also suitable for these purposes. The greatest width of the working member 10 can exceed its length and the smallest width can be smaller than or the same as the length. As a result of this advantageous construction, any dispensed medium flowing downwards on the inside of the jacket 26 can collect in the lower flat shell-like area of the portions 29, 30 and 31, or the lower arm 32, and can be easily removed through opening 35.

In any state, the working member 10 projects with most of its length, or at least substantially completely, over the outer circumference of the unit 2. This is the case at least for the fastening body 9 and the head 20. A ring shoulder, or the like, of the fastening member 9 can also form a stop 40 for stroke limitation, against which the working member 10 strikes in the vicinity of the bottom 27 with the outer circumference of the jacket 26 at the end of the stroke. In each position, the outside of the bottom 27 is close to an outer circumferential surface of the body 9 connected to the stop 40. Accordingly, any tilting loads will not damage the working member 10, and instead, the working member 10 strikes against the stop 40 and/or the circumferential surface. The working member 10 is consequently protected against further deformation, particularly of the bottom 27 and the portion 29.

In accordance with an inventive arrangement, the discharge apparatus, or medium dispenser, can also comprise solely the one-piece working member 10. Working member 10 can have a fastening member for the subsequent, non-destructive, easily detachable connection to a discharge head, the neck of a dropping bottle and the like. The fastening member can be fastened with a plug-in or snap connection oriented radially and/or axially with respect to the axis 11. This can take place particularly in a groove, such as an annular groove of the support 20 with which the fastening members can be connected in a positionally rigid manner. The remaining working member 10 can be moveable with respect to the fastening member, for example, being pivotable about an axis of a film joint or the like, positioned transversely, but laterally displaced with respect to the axis 10. Such a mounting arrangement enables the working member 10 to be swung out of its working position, located on the fastening member with the bottom 27, in a laterally outward direction from the axis 11, into a non-use position. Consequently, the medium can be dispensed from outlet 5 at a random distance from the treating surface, independently of the working member. In this case, the bottom 27 has a passage opening for the outlet projection, the plate-like fastening member being constructed in one piece with the working member 10 or head 20. A resilient snap connection is provided for securing the working member 10 in the working position and/or in the non-use position. The working member can also be provided as a plug-on protective cap for the head 20 or the unit 2, securing the latter against unintentional discharge actuation.

In accordance with the inventive arrangement, a dispenser 1 is provided which provides an annular pressure face 28 spaced from the discharge nozzle 5, which during operation has to be loosely placed against an exposed surface of the object to be sprayed, that is, the treating part. Under pressure load the pressure face expands eccentrically. The pressure face 28 is provided at the end of the jacket 26 of a cap body 10, which can resiliently give way only on a partial section of its entire length extension. The cap body 10 is traversed by openings 34, 39, circumferentially and/or at a bottom, which effect a locally, exactly defined light entry as well as irregular stiffness.

The invention may be embodied in other specific forms without departing from the spirit or essential attributes thereof. Accordingly, reference should be made to the appended claims, rather than to the foregoing specification, as indicating the scope of the invention.

I claim:

1. A jacket for use with a dispenser, the dispenser for discharging media against a treating part, comprising:

a rear jacket portion adapted for engaging the dispenser;

a circumferentially closed contact face defining a front opening for receiving the treating part and an axis transverse to said front opening, said front opening having a first diameter and second diameter transverse to said first diameter, and distinct bending arms connecting said contact face to said rear jacket portion, whereby pressure along said axis against said contact face narrows said first diameter and expands said second diameter.

2. The jacket according to claim 1, wherein said contact face has opposing narrow sides defining said first diameter and opposing wide sides defining said second diameter.

3. The jacket according to claim 2, wherein said bending arms include a first opposing pair of bending arms connecting said opposing narrow sides of the contact face to said rear jacket portion and a second opposing pair of bending arms connecting said opposing wide sides of the contact face to said rear jacket portion.

4. A dispenser for discharging media against a treating part outside and separate from said dispenser comprising:

a support member;

a medium outlet for releasing the media out of and away from said dispenser in a discharge operation;

a discharge feeder for feeding the media towards said medium outlet;

a discharge actuator for expelling the media against the treating part, the treating part having an initial state when not in contact with said dispenser; and, a state altering member for non invasively changing the treating part from the initial state to a treating state and for directing said medium outlet toward the treating part, said state altering member supported by said support member and including:

a circumferentially closed contact face for operationally contacting the treating part, said contact face defining an axis, said contact face being radially displaceable with respect to said axis to prepare the treating part for applying the medium, means for operationally radially displacing said contact face with respect to said axis by exerting a contact pressure against said contact face in a direction of said axis, said displacing means including bending arms.

5. The dispenser according to claim 4, wherein said state altering member is at least partly axially and radially spaced from said medium outlet, said state altering member including a furthest forward member section spaced downstream of said medium outlet and including an edge providing said contact face.

6. The dispenser according to claim 4, wherein said state altering member has a free end including said contact face for contacting the treating part, said contact face being located in and extending substantially uniformly all over an annular zone.

7. The dispenser according to claim 4, wherein said contact face is located forward of said medium outlet, said contact face at least partly radially spaced from said axis by 10 to 20 times a median passage width of said medium outlet, said contact face annularly extending around said axis.

8. The dispenser according to claim 4, wherein said displacing means comprises four circumferentially distributed bending arms.

9. The dispenser according to claim 4, wherein said contact face includes a contact portion for operationally contacting the treating part while substantially directing said medium outlet towards the treating part while spaced therefrom, said contact portion being connected with said dispenser by said bending arms.

10. The dispenser according to claim further comprising a discharge head traversed by said medium outlet, said contact face of said state altering member being made as one part with said discharge head.

11. The dispenser according to claim 4, wherein said contact face is shaped to engage a blepharal eyelid zone around an eyeball, said displacing means stretching the eyelid zone laterally away from the eyeball upon axial pressure of said contact face against said eyelid zone.

12. The dispenser according to claim 4, wherein said discharge feeder includes a thrust piston pump and a casing wall circumferentially enclosing a medium chamber, said casing wall being operationally substantially stiff and dimensionally stable, said thrust piston pump providing said support member, said discharge head being made in one part with said state altering, member.

13. The dispenser according to claim 4, wherein said content face is annularly oval, said contact face including first opposing arcuate sections and second opposing arcuate sections, in a view transverse to said axis said first opposing arcuate sections being concave with a first radius of curvature and said second opposing arcuate sections being convex with respect to the treating part, said second opposing arcuate sections having a second radius of curvature smaller than the first radius of curvature.

14. A dispenser for discharging media against a treating part outside and separate from said dispenser comprising:
   a support member;
   a medium outlet for releasing the media out of and away from said dispenser in a discharge operation;
   discharge feeder for feeding the media towards said medium outlet;
   a discharge actuator for expelling the media against the treating part, the treating part having an initial state when not in contact, with said dispenser; and,
   a state altering member for non invasively changing the treating part from the initial state to a treating state and for directing said medium outlet toward the treating part, said state altering member supported by said support member and including:
      a circumferentially closed jacket wall having rear and front jacket portions, said front jacket portion defining a front opening, said front opening closed by the treating part during said treating state, said jacket wall being traversed by circumferentially distributed openings apart from said front opening and said medium outlet
      a rear bottom wall connected to said rear jacket portion, said jacket wall, bottom wall and front opening bounding a spray chamber, and
      resilient bending arms disposed between said openings, said bending arms longitudinally connecting said rear and front jacket portions.

15. The dispenser according to claim 14, wherein said medium outlet includes an atomizing nozzle and said spray chamber encloses and retains the media when atomized.

16. A dispenser for discharging media against a treating part outside and separate from said dispenser, comprising:
   a support member;
   a medium outlet for releasing the media out of and away from said dispenser in a discharge operation;
   a discharge feeder for feeding the media towards said medium outlet;
   a discharge actuator for expelling the media against the treating part; and
   a state altering member for non invasively changing the treating part from the initial state to a treating state and for directing said medium outlet toward the treating part, said state altering member supported by said support member and including:
      an annular deforming member for radially stressing the treating part upon exertion of contact pressure, said annular deforming member having venting windows and defining a ventilating chamber for ventilating the treating part and the media after releasing the media from said medium outlet, said ventilating chamber including a light chamber for illuminating the treating part when changed to the treating state, the treating part bounding said light chamber.

17. A dispenser for discharging media against a treating part outside and separate from said dispenser comprising:
   a support member;
   a medium outlet for releasing the media out of and away from said dispenser in a discharge operation;
   a discharge feeder for feeding the media towards said medium outlet;
   a discharge actuator for expelling the media against the treating part, the treating part having an initial state when not in contact with said dispenser; and,
   a state altering member for non invasively changing the treating part from the initial state to a treating state and for directing said medium outlet against the treating part, said state altering member supported by said support member and including:
      a circumferentially closed contact face for operationally contacting the treating part, said contact face defining an axis, said contact face being radially displaceable with respect to said axis to prepare the treating part for applying the medium, said contact face having first opposing member sections and second opposing member sections connected to said first opposing member sections, and
      means for operationally radially displacing said first member sections with respect to said axis radially outwardly and for simultaneously displacing said second member sections radially inwardly, said means including bending arms.

18. dispenser for discharging media against a treating part outside and separate from said dispenser comprising:
   a support member;
   medium outlet for releasing the media out of and away from said dispenser in a discharge operation, said medium outlet defining a central outlet axis;
   a discharge feeder for feeding the media towards said medium outlet;
   a discharge actuator for expelling the media against the treating part, the treating part having an initial state when not in contact with said dispenser; and,
   state altering member for non invasively changing the treating part from the initial state to a treating state and for directing said medium outlet against the treating part, said state altering member supported by said support member and including:
      a circumferentially closed contact face for operationally contacting the treating part, said contact face being radially displaceable with respect to said outlet axis to prepare the treating part for applying the medium, said contact face including a contact portion for operationally contacting the treating part while said outlet axis traverses the treating part, and
      a plurality of bearing arms bearing against said contact portion, said bearing arms extending only partly around said outlet axis, said bearing arms being spacedly juxtaposed with respect to said outlet axis.

19. A dispenser for discharging media against a treating part outside and separate from said dispenser comprising:
- a support member;
- a medium outlet for releasing the media out of and away from said dispenser in a discharge operation;
- a discharge feeder for feeding the media towards said medium outlet;
- a discharge actuator for expelling the media against the treating part, the treating part having an initial state when not in contact with said dispenser; and,
- a state altering member for non invasively changing the treating part from the initial state to a treating state and for directing said medium outlet against the treating part, said state altering member supported by said support member and including:
  - a circumferentially closed contact face for operationally contacting the treating part, said contact face defining an axis, said contact face being radially displaceable with respect to said axis to prepare the treating part for applying the medium,
  - bending arms, and
  - a dimensionally stiff actuating head, said actuating head mounted on a base unit and being manually displaceable with respect to said base unit for actuating said discharge feeder, said state altering member directly connecting to said actuating head and being made in one part with said actuating head.

20. The dispenser according to claim 19, wherein said actuating head includes a radial outlet extension, said state altering member having only a single bottom wall directly connected to said actuating head adjacent said outlet extension, said actuating head providing an outermost external head jacket, and said bottom wall providing a circumferential section of said outermost external head jacket.

21. A dispenser for discharging media against a treating part outside and separate from said dispenser comprising;
- a support member;
- a medium outlet for releasing the media out of and away from said dispenser in a discharge operation;
- a discharge feeder for feeding the media towards said medium outlet;
- a discharge actuator for expelling the media against the treating part, the treating part having an initial state when not in contact with said dispenser; and,
- a state altering member for non invasively changing the treating part from the initial state to a treating state and for while directing said medium outlet against the treating part, said state altering member supported by said support member and including:
  - a contact face for operationally contacting the treating part, said contact face defining an axis, said contact face being radially displaceable with respect to said axis to prepare the treating part for applying the medium,
  - a freely projecting forward end portion, said forward end portion being circumferentially closed,
  - a rear end connected to said dispenser, at least in said discharge operation said medium outlet being located closer to said rear end than said front end, and
  - circumferentially distributed arms connecting said forward end portion to said rear end.

22. A dispenser for discharging media against a treating part outside and separate from said dispenser comprising:
- a support member;
- a medium outlet for releasing the media out of and away from said dispenser in a discharge operation;
- a discharge feeder for feeding the media towards said medium outlet;
- a discharge actuator for expelling the media against the treating part, the treating part having an initial state when not in contact with said dispenser; and,
- a state altering member for non invasively changing the treating part from the initial state to a treating state and for directing said medium outlet against the treating part, said state altering member supported by said support member and including:
  - a circumferentially closed contact face for operationally contacting the treating part, said contact face defining an axis, said contact face being radially displaceable with respect to said axis to prepare the treating part for applying the medium,
  - bending arms, and
  - first opposing member sections and second opposing member sections laterally distributed around said axis, when commonly stressed said first and second opposing member sections being deflected along respective first and second motion paths, said first motion path of said first opposing member sections being longer than said second motion path of said second opposing member sections.

* * * * *